United States Patent [19]

Horn et al.

[11] 4,128,569

[45] Dec. 5, 1978

[54] CONTINUOUS MANUFACTURE OF ORGANIC ISOCYANATES

[75] Inventors: Peter Horn, Hirschberg; Waldemar Koehler, Frankenthal; Rolf Bittler, Heidelberg, all of Fed. Rep. of Germany

[73] Assignee: BASF Aktiengesellschaft, Ludwigshafen, Fed. Rep. of Germany

[21] Appl. No.: 797,814

[22] Filed: May 17, 1977

[30] Foreign Application Priority Data

May 31, 1976 [DE] Fed. Rep. of Germany ....... 2624285

[51] Int. Cl.$^2$ .......................................... C07C 118/02
[52] U.S. Cl. ............................................. 260/453 PH
[58] Field of Search ................................. 260/453 PH

[56] References Cited

U.S. PATENT DOCUMENTS

| | | | |
|---|---|---|---|
| 2,822,373 | 2/1958 | Beck | 260/453 PH |
| 3,781,320 | 12/1973 | Irwin | 260/453 PH |
| 3,829,458 | 8/1974 | Horn et al. | 260/453 PH |

Primary Examiner—Dolph H. Torrence
Attorney, Agent, or Firm—Keil, Thompson & Shurtleff

[57] ABSTRACT

A process for the continuous manufacture of organic monoisocyanates, diisocyanates and/or polyisocyanates from the corresponding organic amines and phosgene in the presence of inert organic solvents, with recycling of the reaction mixture, wherein the streams of liquid, consisting of the recycle stream and the amine feed solution, are fed to the reaction mixture at a rate such that an energy dissipation density of from 5 to 1,000 kJoule per m$^3$ of recycled reaction mixture plus amine feed solution is generated in the mixing and reaction zone.

9 Claims, 1 Drawing Figure

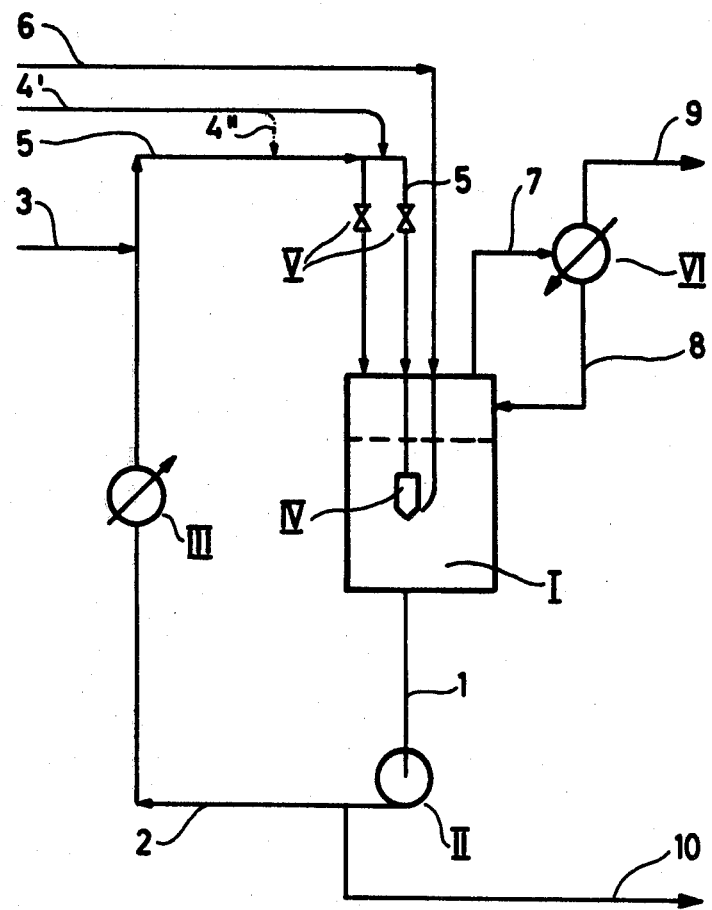

CONTINUOUS MANUFACTURE OF ORGANIC ISOCYANATES

The present invention relates to a process for the manufacture of organic isocyanates from organic primary amines and phosgene in the presence of inert organic solvents, with partial recycling of the reaction mixture, the starting components being fed to the reaction mixture in such a way that an energy dissipation density of from 5 to 1,000 kJoule per m$^3$ of recycled reaction mixture plus amine feed solution is generated in the mixing and reaction zone.

The manufacture of isocyanates from primary amines and phosgene has been disclosed. Depending on the nature of the amines, the reaction is carried out either in the gas phase or in the liquid phase, either batchwise or continuously (W. Siefken, Liebigs Ann. 562, 75 (1949)).

The conventional processes suffer from numerous disadvantages. If low temperatures are used for the initial phosgenation (cold phosgenation), the liberation of large amounts of phosgene whilst raising the temperature to the final phosgenation temperature (hot phosgenation temperature) presents a problem which is difficult to deal with and which is further aggravated by the high toxicity of phosgene. Low temperature processes also suffer from a further disadvantage, namely that the rate of reaction is relatively low, so that large reaction volumes have to be handled. In the two-stage processes, the end product and the carbamyl chloride formed as an intermediate in the first stage can react with some of the starting amine to form substituted ureas and polyureas or other undesirable products. It is true that a number of the conventional processes of manufacture have achieved considerable success in industrial operation, but all these methods suffer from the disadvantage that excessive amounts of polymers and other undesirable by-products are formed. The formation of the by-products can substantially reduce the yield of isocyanate and/or the product quality.

U.S. Pat. No. 2,822,373 has disclosed a process which operates continuously under superatmospheric pressure and at an elevated temperature, in which a part of the reaction solution is recycled and the phosgene solution is mixed with an amine solution before entering the reaction vessel. In this process, a certain turbulence must be set up at the point of combination of the two solutions. However, blockages can easily occur in the flow tube, preventing turbulence.

According to the disclosure of U.S. Pat. No. 3,829,458, organic isocyanates are manufactured continuously from primary organic amines and phosgene in an inert organic solvent in one or more packed reaction vessels, preferably with recycling of the reaction mixture, under conditions of what is called transition flow. Using this relatively simple process, isocyanates can be manufactured with a high spacetime yield. However, in this process the introduction of the amines into the phosgene-containing reaction solution again presents certain difficulties, since with some amines optimum intermixing of the starting components can only be achieved with difficulty. If, on the other hand, the reactants are not intermixed adequately, amine hydrochlorides and ureas are formed as by-products; these in part deposit on the packing and can lead to blockages of the packed columns.

It is an object of the present invention to provide a continuous process for the manufacture of isocyanates in which the starting components, namely the amine or amine solution and phosgene, are intermixed rapidly and under optimum conditions, in which the conversion to isocyanates takes place completely in a short time, so that the formation of by-products is virtually completely suppressed, and which gives high yields of isocyanate and end products of high purity.

This object is achieved by a process for the manufacture of an organic isocyanate from an organic amine and phosgene in the presence of an organic solvent, with partial recycling of the reaction solution, wherein the phosgene is mixed with the reaction solution being recycled and the resulting phosgene-containing reaction solution and the amine feed are fed to a mixing and reaction zone under conditions such that in this zone an energy dissipation density of from 5 to 1,000 kJoule per m$^3$ of phosgene-containing reaction solution plus amine feed is generated.

The process according to the invention has the advantage that the starting components are thoroughly mixed in a very simple manner and in an extremely short time, the phosgenation of the amines and the formation of the isocyanates takes place with residence times of from 10 to 180 minutes, and the isocyanates are obtained in high purity and in yields of from 88 to 98% by weight, based on the amine employed.

The process according to the invention is quite generally applicable to the manufacture of organic isocyanates which can be obtained by reacting amines with phosgene. For example, monoisocyanates, diisocyanates and/or polyisocyanates can be manufactured from the corresponding organic monoamines, diamines and polyamines.

Suitable organic monoamino compounds have the formula R-NH$_2$, where R is an unsubstituted or substituted monovalent aliphatic, cycloaliphatic or, preferably, aromatic radical of 1 to 20, preferably of 6 to 12, carbon atoms. Examples are aliphatic monoamines, e.g. methylamine, ethylamine, butylamine, octylamine and stearylamine, cycloaliphatic monoamines, e.g. cyclohexylamine, and especially aromatic monoamines, e.g. aniline, toluidines, naphthylamines, chloroanilines and anisidines.

Preferably, however, the diisocyanates and polyisocyanates, which are of importance for the industrial manufacture of polyurethanes, are manufactured from the corresponding diamines and polyamines by the new process. Suitable diamino compounds have the formula H$_2$N-R'-NH$_2$, where R' is a divalent aliphatic or cycloaliphatic radical of 2 to 18, especially of 4 to 12, carbon atoms or, preferably, is a divalent aromatic radical which consists of one or more aromatic nuclei of 6 to 18 carbon atoms, directly linked to one another or linked via divalent bridge members, e.g. —O—, —SO$_2$—, —CH$_2$— and

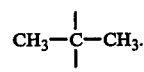

The diamino compounds and/or polyamino compounds may be used individually or as mixtures.

Examples of such aliphatic, cycloaliphatic or, especially, aromatic diamino compounds are 1,4-diaminobutane, 1,10-diaminodecane, 1,12-diamino-dodecane, 1,4-diamino-cyclohexane, 1,6-diaminohexane and 4,4'-diamino-dicyclohexyl, preferably 4,4'-diamino-diphenyl, 1,4- and 1,3-phenylenediamine, 1,5- and 1,8-naphthylenediamine, and especially 2,4- and 2,6-toluylenediamine and 2,2'-, 2,4'- and 4,4'-diaminodiphenylmethane.

Examples of suitable polyamines are tri-(p-aminophenyl)-methane, 2,4,6-triamino-toluene and condensation products which are obtained from substituted or unsubstituted aniline derivatives and aldehydes or ketones in the presence of acids, e.g. polyphenyl-polymethylene-polyamines.

The process according to the invention is particularly suitable for the manufacture of aromatic diisocyanates and/or polyisocyanates from the corresponding amines and is therefore preferentially used for this purpose.

The other starting component used is phosgene. The reaction may be carried out with gaseous or liquid phosgene as such or diluted with gases which are inert under the reaction conditions, e.g. nitrogen, carbon monoxide and the like. The molar ratio of amine to phosgene is advantageously such as to provide from 1 to 10 moles, preferably from 1.3 to 4 moles, of phosgene in the reaction mixture per mole of $NH_2$ group.

Suitable inert organic solvents are compounds in which the amines and the phosgene are at least partially soluble, i.e., soluble to the extent of at least 5%, but preferably to the extent of from 50 to 100%. Chlorinated aromatic hydrocarbons, e.g. chlorobenzene, o-dichlorobenzene, p-dichlorobenzene, trichlorobenzenes, the corresponding toluenes and xylenes, chloroethylbenzene, monochlorodiphenyl, α- and β-naphthyl chloride and dialkyl phthalates, e.g. diethyl isophthalate, have proved particularly suitable. The solvents may be used individually or as mixtures. Advantageously, the solvent used has a lower boiling point than the isocyanate to be manufactured, so that the solvent can readily be separated from the isocyanate by distillation. The amount of solvent is advantageously such that the reaction mixture has an isocyanate content of from 2 to 40% by weight, preferably from 5 to 20% by weight, based on the total weight of the reaction mixture.

The amines may be used undiluted or as solutions in organic solvents. In particular, amine solutions with an amine content of from 5 to 40% by weight, preferably from 10 to 30% by weight, based on the total weight of the solution, are used.

The reaction is advantageously carried out at from 90° to 220° C., preferably from 120° to 180° C., and at pressures of from 1 to 10 bars, preferably from 1 to 3 bars. The temperature used in the process according to the invention is above the decomposition point of the carbamyl chloride formed as an intermediate product of the reaction of phosgene with amine. The only upper limits on the pressure are set by technical considerations and, at times, safety considerations, but higher pressures than those stated do not produce any further increase in yield.

In carrying out the process according to the invention, the reaction solution, which consists of solvent, dissolved isocyanate, phosgene, hydrogen chloride and phosgenation by-products, is recycled from a reaction chamber, by means of a circulating pump, back into the reaction chamber, part or all of the recycled reaction solution being introduced through a nozzle. Fresh phosgene, with or without phosgene-containing solvent, is admixed to the reaction solution by introduction into the recycle stream; in an advantageous embodiment of the process the fresh phosgene is introduced into the reaction solution after the part-stream which does not pass through the nozzle has been branched off. This ensures that the total amount of fresh phosgene enters the reaction chamber via the nozzle. The amine solution is fed into the reaction chamber. A volume of reaction solution corresponding to the total liquid feed is withdrawn from the cycle as a product solution, for further working up. A venting space is required in the recycling system, in order to allow the hydrogen chloride liberated by the phosgenation to escape.

The dimensions of the reaction chamber are preferably such as to make it possible to achieve mean residence times of from about 10 minutes to 3 hours, more preferably from 15 minutes to 2 hours, based on the volume of product solution discharged.

The amount of reaction solution recycled is such that the volume ratio of the total amount of recycled reaction solution plus added fresh phosgene plus any added phosgene-containing solvent to the amount of amine feed solution is from 300:1 to 1:1, preferably from 100:1 to 5:1.

The part of the reaction mixture, consisting of recycled reaction solution and freshly fed-in phosgene, with or without added phosgene-containing solvent, which is fed into the reaction chamber through the nozzle may amount to from 5 to 100%, preferably from 20 to 100%, of the total reaction mixture entering the reaction chamber. The part of the reaction mixture which is passed through the nozzle undergoes severe acceleration, so that it issues from the nozzle as a drive jet, with a high velocity relative to the contents of the reaction chamber. As a result of feeding up to the nozzle exit and of introducing the amine solution close to the nozzle exit, the amine solution is thoroughly mixed with the reaction solution in an extremely short time.

In order to achieve optimum reaction rates and optimum yields of isocyanate it is essential to the invention that an energy dissipation density of from 5 to 1,000, preferably from 50 to 400 kJoule per $m^3$ of recycled reaction mixture plus amine feed solution prevails in the mixing and reaction zone. This energy dissipation density is generated if the part of the reaction mixture which passes through the nozzle is fed to the mixing and reaction zone at a nozzle exit velocity of from 1 to 40 m/sec., preferably from 5 to 30 m/sec., and the amine or the amine solution is fed to the mixing and reaction zone through the amine feed tube with an exit velocity of from 0.3 to 30 m/sec., preferably from 0.5 to 3 m/sec. The mixing and reaction zone is characterized by the mass flow of the reaction mixture fed in and the amine solution fed in, and the combined liquid streams must exhibit the above energy dissipation densities. The mixing and reaction zone has a mean diameter which corresponds to from 3 to 30 times, preferably from 10 to 25 times, the mean diameter of the drive jet of the reaction mixture. The mean diameter of the drive jet means the diameter of a circle of equal area to that of the cross-sectional areas of the nozzle orifices, for example of annular nozzles or slot nozzles, of the mixing zone. The mixing and reaction zone may be of constant cross-section or the cross-section may alter in the direction of flow. The said zone can have various shapes, the shape advantageously being suited to the shape of nozzle used. In general, tubes in the shape of a segment of a cone or, preferably, cylindrical tubes are used. In the latter case, the length should be from 1 to 20 times, preferably from 1.5 to 5 times, the diameter. If the mixing and reaction zone does not have a circular cross-section, or if its cross-section is not constant over its length, the length of the zone should be from 1 to 20 times, preferably from 1.5 to 5 times, the hydraulic diameter. This latter term means the diameter of a cylindrical tube which, at equal throughput and equal length, results in the same pressure loss as the mixing and reaction zone in question.

The mixing and reaction zone is part of the reaction chamber, the size of which is characterized by the above mean residence times. The reaction chamber need not necessarily be constructed as a separate reaction vessel but can instead, for example, also be constructed as a reaction tube and form part of the recycle pipeline system.

The venting space which allows the hydrogen chloride formed during the phosgenation to escape is advantageously, but not necessarily, located above the reaction chamber. If a separate reaction vessel is used as the reaction chamber, it is advantageous to use the upper part of this vessel as the venting space and to withdraw the hydrogen chloride gas, containing phosgene and solvent vapors, at that point. Instead, it is however also possible to provide a separate venting vessel in the recycling system, downstream from the reaction chamber.

A preferred embodiment of the process of manufacture according to the invention is explained once again, in greater detail, with reference to the accompanying drawing.

In the drawing the numerals denote the following:
I — Reaction vessel
II — Circulating pump
III — Heat exchanger
IV — Drive jet nozzle
V — Valves for dividing up the recycled reaction mixture
VI — Condenser
1. — Reaction solution discharge line
2. — Recycling line for reaction solution
3. — Feed line for phosgene-containing solvent
4' and 4" — feed line for phosgene
5. — Feed line for the reaction mixture consisting of reaction solution (2) and feed steams (3) and (4') and (4")
6. — Feed line for amine or amine solution
7. — Vapor discharge line for hydrogen chloride, phosgene and solvent
8. — Recycling line for condensed solvent and phosgene
9. — Discharge line for phosgene and hydrogen chloride
10. — Discharge line for isocyanate solution.

Reaction solution is pumped, via a circulating pump (II) and a heat exchanger (III), through the line (1) from the reaction vessel (I) which is completely or preferably partially filled with reaction solution but contains at least sufficient reaction solution that the drive jet nozzle (IV) is completely immersed in the reaction solution; at the same time fresh phosgene is admixed to the reaction solution through the line (4"), but preferably (4'), and phosgene-containing solvent may or may not be admixed through the line (3). The reaction mixture, consisting of the reaction solution (1) and the admixed streams (III) and, if relevant, (4") is divided by means of the line (5), using the two valves (V.) A part of the mixture can be recycled directly to the reaction vessel whilst the other — preferably after the introduction of fresh phosgene through line (4') - is fed to the nozzle (IV) and, greatly accelerated, enters the reaction solution in the form of a drive jet. The amine solution or the amine is introduced through the line 6 and is thoroughly mixed with, and caused to react with, the reaction mixture in the mixing and reaction zone. The volatile constituents, namely hydrogen chloride, excess gaseous phosgene and solvent vapor, escape through the discharge line (7) into a condenser (VI). There, the solvent and the greater part of the phosgene are condensed and recycled through the solvent-phosgene recycle line (8) into the reaction vessel (I), whilst the gaseous hydrogen chloride/phosgene mixture is discharged through the line (9) and separated in accordance with conventional methods, and the phosgene is isolated. The isocyanate-containing reaction solution manufactured in accordance with the process of the invention is taken off through the line (10) and worked up by means of conventional methods of purification.

The process according to the invention is illustrated by the Examples which follow:

EXAMPLES

The experimental arrangement is shown in the drawing. A heated 2,000 ml glass autoclave of 12 cm internal diameter is used as a reaction vessel (I). The reaction solution is pumped through a heat exchanger (III) by means of a centrifugal pump (II). Downstream from the heat exchanger (III), phosgene-containing solvent (3) from the working-up of the product solution, and liquid fresh phosgene (4') are each introduced into the reaction solution through a T-piece. The phosgene-containing reaction mixture obtained is completely or partially (depending on the setting of the valves (V)) injected through a drive jet nozzle, which has an internal diameter of 0.9 - 1.8 mm and dips into the reaction solution in the reaction vessel (I). The amine solution is fed into the drive jet through a feed tube of from 0.5 to 1.0 mm diameter. At the beginning of the reaction, the reaction vessel (I) and the recycle stream are primed with 1,000 ml of phosgene-saturated o-dichlorobenzene.

The amines used to manufacture the isocyanates, the flow rates, reaction conditions and experimental results are summarized in the Table which follows.

TABLE

| Examples | | 1 | 2 | 3 | 4 | 5 | 6 |
|---|---|---|---|---|---|---|---|
| Diameter of the drive jet nozzle | [mm] | 0.9 | 1.8 | 1.0 | 1.8 | 1.0 | 1.0 |
| Diameter of the amine feed line | [mm] | 0.5 | 0.5 | 1.0 | 1.0 | 1.0 | 1.0 |
| Liquid volume in the reaction vessel | [mm] | 1,000 | 1,000 | 1,000 | 1,000 | 1,000 | 1,000 |
| Amine | | Mixture of 2,4- and 2,6-toluyl-enediamine (80:20) | as for Example 1 | as for Example 1 | 1,5-di-amino-naphtha-lene | p-phenyl-ene-diamine | mixture of di-aminodiphenyl-methane and polyphenyl-poly-methylene-poly-amines |
| Amine content in the base solution | [%] | 20 | 10 | 20 | 10 | 20 | 20 |
| Temperature of the | [° C] | 85 | 85 | 90 | 130 | 75 | 60 |

TABLE-continued

| Examples | | 1 | 2 | 3 | 4 | 5 | 6 |
|---|---|---|---|---|---|---|---|
| base solution | | | | | | | |
| Feed rate of base solution (6) | [g/h] | 1,000 | 1,000 | 1,000 | 1,000 | 1,000 | 1,200 |
| Feed rate of phosgene (4') | [g/h] | 470 | 250 | 550 | 472 | 710 | 300 |
| Amount of reaction solution recycled by circulating pump (2) | [ml/h] | 40,000 | 45,000 | 40,000 | 45,000 | 35,000 | 30,000 |
| Flow rate through drive jet nozzle (IV) | [ml/h] | 40,000 | 45,000 | 20,000 | 15,000 | 35,000 | 30,000 |
| Linear velocity of drive jet | [m/s] | 19 | 5.3 | 7.7 | 5.8 | 13.5 | 11.6 |
| Velocity of amine feed | [m/s] | 1.5 | 1.5 | 0.39 | 0.39 | 0.39 | 0.46 |
| Temperature of reaction vessel | [° C] | 150 | 140 | 155 | 150 | 160 | 150 |
| Pressure in reaction vessel | [bar] | 2 | 2 | 3 | 5 | 3 | 2.5 |
| Pressure in the feed line (5) upstream from drive jet nozzle (IV) | [bar] | 5 | 3.8 | 6 | 7 | 4 | 4.5 |
| Solvent/phosgene recycle (8) from condenser (VI); 85% strength $COCl_2$ | [g/h] | 1,000 | 500 | 1,200 | 1,100 | 1,300 | 2,600 |
| Phosgene-containing solvent (4); 10% by weight of phosgene | [g/h] | 500 | | 500 | 500 | 600 | 600 | 1,000 |
| Running time | [h] | 36 | 24 | 28 | 48 | 22 | 36 |
| Yield of isocyanate | [%] | 98 | 95 | 88 | 92 | 94 | — |
| Isocyanate | | | Mixture of 2,4- and 2,6-toluene diisocyanate | | | 1,5-Naphthylene diisocyanate iso- | 1,4-phenylene diisocyanate | crude MDI |

We claim:

1. In a process for the continuous manufacture of an organic isocyanate from an organic amine and phosgene in the presence of an organic solvent, wherein the organic isocyanate, organic amine, phosgene and organic solvent are conducted into a reaction chamber to form a reaction solution and a portion of the reaction solution is recycled, the improvement comprising:
   mixing phosgene with the recycled portion of the reaction solution,
   feeding the phosgene-containing recycled portion of the reaction solution to a nozzle, the exit of said nozzle extending below the surface of the reaction solution contained in the reaction chamber,
   accelerating the phosgene-containing recycled portion of the reaction solution through the nozzle such that the recycled reaction solution issues from the nozzle as a drive jet having a velocity of from 1 to 40 m/sec thereby forming a mixing and reaction zone within the reaction chamber,
   while simultaneously feeding organic amine or amine solution at a velocity of from 0.3 to 30 m/sec to the drive jet of the recycled phosgene-containing reaction solution in the mixing and reaction zone, so that the volume ratio of the total amount of phosgene-containing recycled reaction solution to the amount of organic amine or amine solution is from 300:1 to 1:1,
   whereby an energy dissipation density of from 5 to 1000 kJoule per m³ of phosgene-containing reaction solution plus amine feed is generated in the mixing and reaction zone.

2. A process as set forth in claim 1, wherein from 5 to 100% of the phosgene-containing reaction solution obtained by mixing the reaction solution being recycled and phosgene is fed to the mixing and reaction zone at a velocity of from 1 to 40 m/sec. and the amine feed is fed to the said zone at a velocity of from 0.3 to 30 m/sec.

3. A process as set forth in claim 1, wherein an aromatic monoamine, diamine or higher polyamine is used as organic amine.

4. A process as claimed in claim 3, wherein 4,4'-diaminodiphenyl, 1,4- and/or 1,3-phenylenediamine, 1,5- and/or 1,8-naphthylenediamine, 2,4- and/or 2,6-toluylenediamine, 2,2'-, 2,4'- and/or 4,4'-diaminodiphenylmethane, or a mixture of one or more diaminodiphenylmethanes and one or more polyphenyl-polymethylene-polyamines is used as organic amine.

5. A process as set forth in claim 1, wherein the amine feed is composed of a liquid mixture of the amine and an organic solvent.

6. A process as set forth in claim 1, wherein the reaction mixture being recycled is divided into two parts, the phosgene is added to one part and the resulting mixture is introduced into the mixing and reaction zone as the drive jet, and the other part is introduced separately into the mixing and reaction zone.

7. A process as set forth in claim 1, wherein the reaction is carried out in a reaction chamber of dimensions such that the mean residence time is 15 minutes to 2 hours, based on the volume of product solution discharged.

8. A process as set forth in claim 1, wherein phosgene-containing solvent derived from the working up of the product is mixed with the reaction mixture being recycled, in addition to fresh phosgene, to form the phosgene-containing reaction solution.

9. A process as set forth in claim 1, wherein the energy dissipation density in the mixing and reaction zone is from 50 to 400 kJoule per m³ of phosgene-containing reaction solution plus amine feed.